United States Patent
Qian

(10) Patent No.: US 9,630,913 B2
(45) Date of Patent: Apr. 25, 2017

(54) NITRO-CONTAINING BISOXIME ESTER PHOTOINITIATOR AND PREPARATION METHOD AND USE THEREOF

(71) Applicants: CHANGZHOU TRONLY NEW ELECTRONIC MATERIALS CO., LTD., Jiangsu (CN); CHANGZ PIONEER ELECTRONIC MATERIALS CO., LTD., Jiangsu (CN)

(72) Inventor: Xiaochun Qian, Jiangsu (CN)

(73) Assignees: Changzhou Tronly New Electronic Materials Co., Ltd., Jiangsu (CN); Changzhou Tronly Advanced Electronic Materials Co., Ltd., Jiangsu (CN)

( * ) Notice: Subject to any disclaimer, the term of this patent is extended or adjusted under 35 U.S.C. 154(b) by 0 days.

(21) Appl. No.: 15/116,356

(22) PCT Filed: Mar. 17, 2015

(86) PCT No.: PCT/CN2015/074368
§ 371 (c)(1),
(2) Date: Aug. 3, 2016

(87) PCT Pub. No.: WO2015/139604
PCT Pub. Date: Sep. 24, 2015

(65) Prior Publication Data
US 2016/0376225 A1  Dec. 29, 2016

(30) Foreign Application Priority Data

Mar. 18, 2014 (CN) .................. 2014 1 0101531

(51) Int. Cl.
| | | |
|---|---|---|
| C07C 251/66 | (2006.01) | |
| C07C 319/20 | (2006.01) | |
| C07D 335/12 | (2006.01) | |
| C07D 409/14 | (2006.01) | |
| C07C 249/04 | (2006.01) | |
| C07D 311/82 | (2006.01) | |
| C07D 307/91 | (2006.01) | |
| C07C 323/63 | (2006.01) | |
| C07D 333/76 | (2006.01) | |
| C07C 323/47 | (2006.01) | |
| C07D 209/88 | (2006.01) | |
| C08F 2/50 | (2006.01) | |
| G03F 7/004 | (2006.01) | |
| G03F 7/027 | (2006.01) | |
| C08F 265/06 | (2006.01) | |
| G03F 7/031 | (2006.01) | |

(52) U.S. Cl.
CPC .......... *C07C 251/66* (2013.01); *C07C 323/47* (2013.01); *C07D 209/88* (2013.01); *C07D 307/91* (2013.01); *C07D 333/76* (2013.01); *C08F 2/50* (2013.01); *C08F 265/06* (2013.01); *G03F 7/004* (2013.01); *G03F 7/027* (2013.01); *G03F 7/031* (2013.01); *C07C 2101/08* (2013.01); *C07C 2101/14* (2013.01)

(58) Field of Classification Search
None
See application file for complete search history.

(56) References Cited

FOREIGN PATENT DOCUMENTS

| | | |
|---|---|---|
| CN | 1514845 A | 7/2004 |
| CN | 101508744 A | 8/2009 |
| CN | 101528694 A | 9/2009 |
| CN | 102775527 A | 11/2012 |
| CN | 103130833 A | 6/2013 |
| CN | 103130919 A | 6/2013 |
| JP | 2009179619 A | 8/2009 |

OTHER PUBLICATIONS

CAPLUS printout of Foreign Patent No. JP50012047, published on Feb. 7, 1975.*

* cited by examiner

*Primary Examiner* — Matthew Coughlin
*Assistant Examiner* — Po-Chih Chen
(74) *Attorney, Agent, or Firm* — Cesari and McKenna, LLP

(57) ABSTRACT

This present invention discloses a nitro-containing bisoxime ester photoinitiator having a structure represented by general formula (I). This photoinitiator has excellent application performances in terms of storage stability, photosensitivity, developability, pattern integrity, etc., and it has good adaptability to single-wavelength UV-LED light sources and exhibits a photosensitive property, which is obviously superior to those of existing photoinitiators, under the irradiation of UV-LEDs.

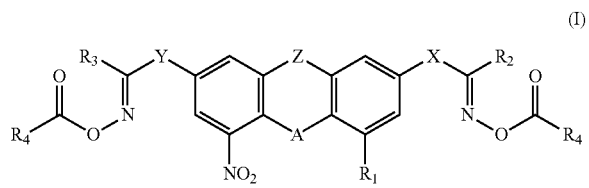

(I)

8 Claims, No Drawings

NITRO-CONTAINING BISOXIME ESTER PHOTOINITIATOR AND PREPARATION METHOD AND USE THEREOF

CROSS REFERENCE TO RELATED APPLICATIONS

This application is the National Stage of International Application No. PCT/CN2015/074368, filed on Mar. 17, 2015, which claims priority to Chinese Application No. 201410101531.X, filed on Mar. 18, 2014. The contents of both applications are hereby incorporated by reference in their entirety.

TECHNICAL FIELD

This invention pertains to the technical field of photoinitiators, and particularly to a nitro-containing bisoxime ester photoinitiator and a preparation method and a use thereof.

BACKGROUND ART

The use of compounds having groups of carbazolyl, diphenyl sulfide group, and the like and being connected with an oxime ester structure as photoinitiators has been well known in the art, and the design and the synthesis of novel oxime ester initiators, particularly those having better application performances, are always hot spots in the field of photocuring in recent years. For example, Chinese patent documents having Publication Nos. CN1514845A, CN101508744A, CN101528694A, etc., disclose a variety of oxime ester photoinitiators, and these products have good photosensitivity, storage stability, etc., and satisfy and improve the demand of development of photocurable compositions to some extent.

However, it is found in practical application that there are extremely serious limits for these existing oxime ester photoinitiators in selection of suitable excitation light sources, similarly to conventional photoinitiators. Typically, they can be activated to function only under the irradiation of a broad-spectrum ultraviolet light (UV). Nowadays, light sources for activating photocuring systems (i.e., emitting the broad-spectrum ultraviolet light described above) are mainly high-pressure mercury lamps, and the emission spectra thereof center on 436 nm, 405 nm, 365 nm, 313 nm, and 302 nm, and most of existing photoinitiators have good absorption at the short wavelengths described above. However, such light sources have obvious drawbacks such as large energy consumption, long preheating time, being not environmentally friendly, etc., and they are limited more and more in applications and are being gradually eliminated by the market.

UV-LED light sources have the advantages of high light purity, low energy consumption, simple operation, being environmentally friendly, etc. At present, they have been widely used in fields of civil applications and have been gradually known in the industry of photocuring. Compared to UV mercury lamp systems, UV-LEDs have great advantages in terms of energy saving and emission reduction, improvement of production efficiency, expansion of application range of the photocuring technology, etc. The mode of UV-LED excitation is very promising to become a next mainstream trend of development of the photocuring technology.

Since the UV-LED light source itself has a relatively narrow light emission spectrum, the application performances exhibited by existing photoinitiators under its excitation are hardly satisfactory. Therefore, it is appears to be important to research and develop a photoinitiator having an excellent photosensitive property matched with UV-LED light sources.

SUMMARY OF THE INVENTION

With respect to the shortages of existing photoinitiators, an object of this invention is to provide an oxime ester photoinitiator, which exhibits excellent application performances under both mercury lamps and UV-LED lamps. By elaborate design and modification of the chemical structure, a compound containing a nitro group and a bisoxime ester structure is designed and synthesized. This product has excellent performances in terms of storage stability, photosensitivity, developability, pattern integrity, etc., and particularly, it exhibits a photosensitive property, which is obviously superior to those of existing photoinitiators, under the irradiation of UV-LEDs having single wavelengths (such as 395 nm).

In order to achieve the technical effect described above, the technical solution used in this invention is as follows:

a nitro-containing bisoxime ester photoinitiator, having a structure represented by general formula (I):

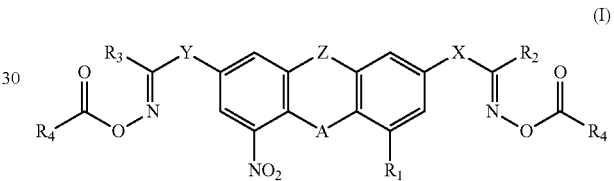

wherein,

X and Y each independently represent a carbonyl (—CO—) or a single bond;

Z is blank (i.e., two benzene rings on the left and on the right are connected with each other only by A), a single bond, or a $C_1$-$C_5$ alkylene;

A is O, S, or a $R_5N$— group, wherein $R_5$ represents hydrogen, a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group;

$R_1$ represents halogen, a nitro group, a hydroxy group, a carboxyl group, a sulfonic acid group, an amino group, a cyano group, or an alkoxy group, or a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group optionally substituted with one or more group selected from the group consisting of halogen, a nitro group, a hydroxy group, a carboxyl group, a sulfonic acid group, an amino group, a cyano group, and an alkoxy group;

$R_2$ and $R_3$ each independently represent hydrogen, a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, or a $C_7$-$C_{20}$ of aralkyl group, and optionally, hydrogen in the above groups may be substituted with a group selected from the group consisting of halogen, a nitro group, a hydroxy group, a carboxyl group, a sulfonic acid group, an amino group, a cyano group, and an alkoxy group;

$R_4$ represents a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_3$-$C_{20}$ heteroaryl group, or a $C_6$-$C_{20}$ aryl group, and optionally, hydrogen in the above groups may be substituted with a group selected from the group consisting of halogen, a phenyl group, a nitro group, a hydroxy group, a carboxyl group, a sulfonic acid group, an amino group, a cyano group, and an alkoxy group.

As a preferable solution of this invention, in the nitro-containing bisoxime ester photoinitiator represented by the general formula (I) described above:

Z is blank, a single bond, a methylene group, an ethylene, or a propylene group;

A is O, S, or a $R_5N$— group, wherein $R_5$ represents hydrogen, a $C_1$-$C_{10}$ linear or branched alkyl group, a $C_3$-$C_{15}$ cycloalkyl group, or a $C_4$-$C_{15}$ cycloalkylalkyl group;

$R_1$ represents hydrogen, halogen, a nitro group, or a $C_1$-$C_{15}$ linear or branched alkyl group;

$R_2$ and $R_3$ each independently represent hydrogen, a $C_1$-$C_{15}$ linear or branched alkyl group, a $C_3$-$C_{15}$ cycloalkyl group, a $C_4$-$C_{15}$ cycloalkylalkyl group, a $C_4$-$C_{15}$ alkylcycloalkyl group, or a $C_7$-$C_{15}$ of aralkyl group, and optionally, hydrogen in the above groups may be substituted with a group selected from the group consisting of halogen, a nitro group, and an alkoxy group;

$R_4$ represents a $C_1$-$C_{10}$ linear or branched alkyl group, a $C_3$-$C_{10}$ cycloalkyl group, a $C_4$-$C_{10}$ cycloalkylalkyl group, a $C_4$-$C_{10}$ alkylcycloalkyl group, a $C_3$-$C_{10}$ heteroaryl group, or a $C_6$-$C_{10}$ aryl group.

As a preferable solution of this invention, the nitro-containing bisoxime ester photoinitiator described above is selected from the group consisting of the following structures:

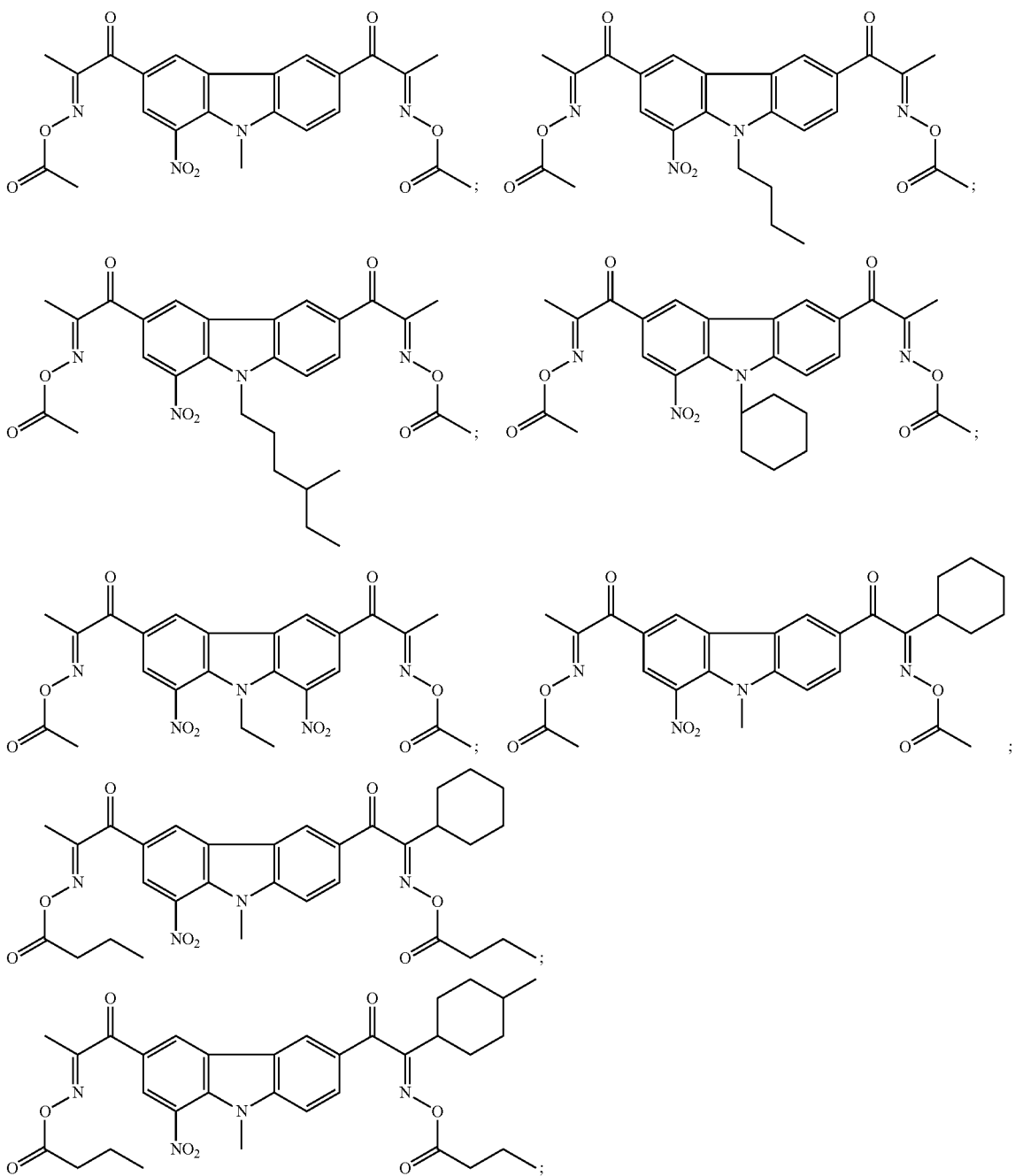

-continued
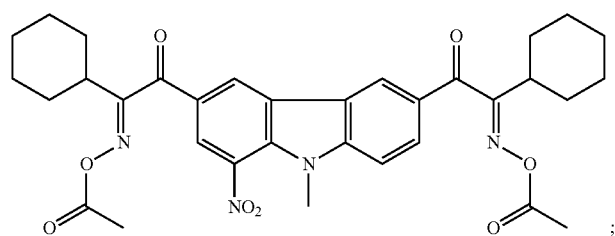
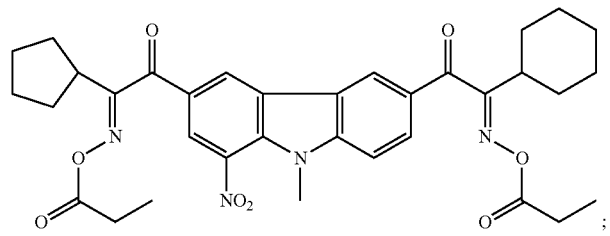
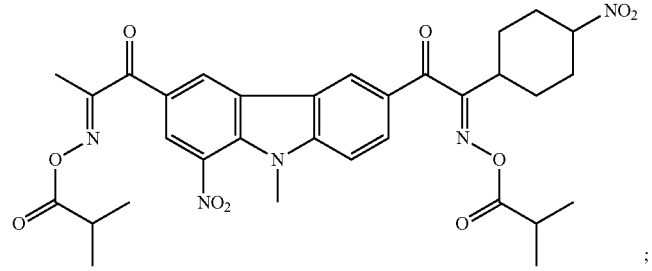
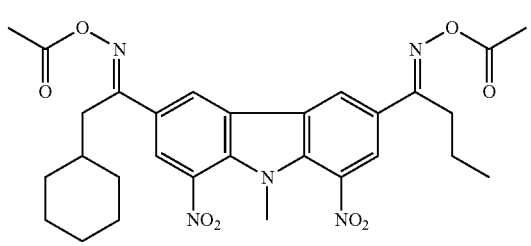
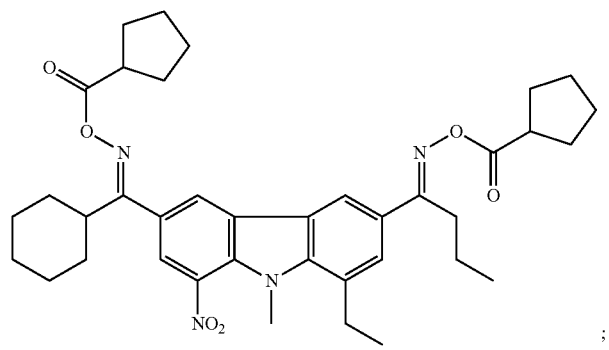
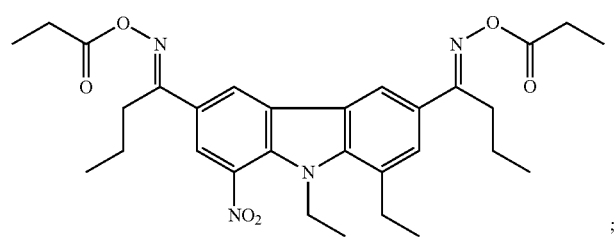
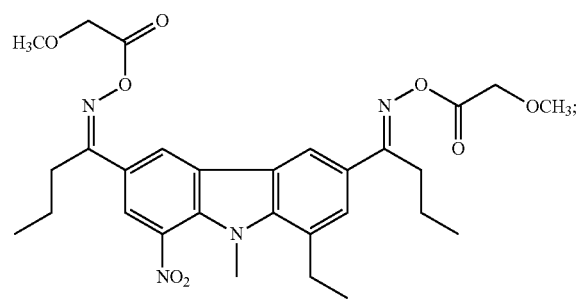

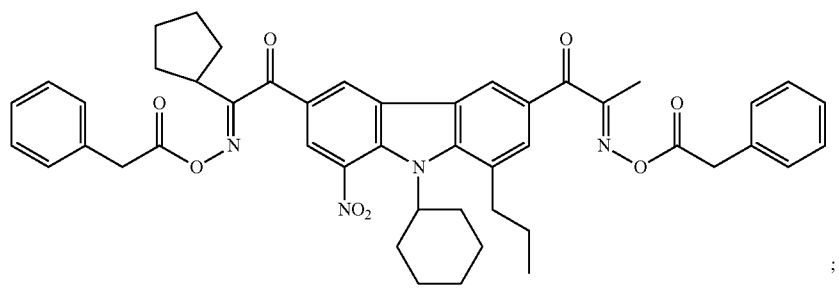
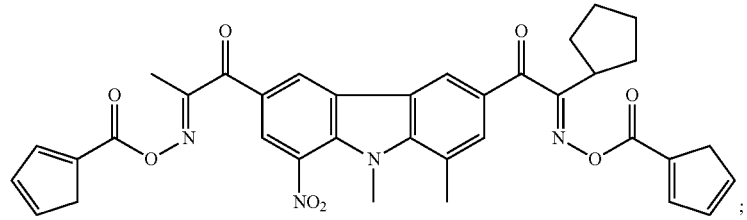
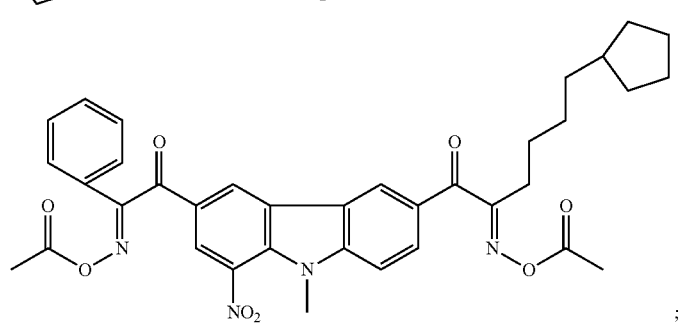
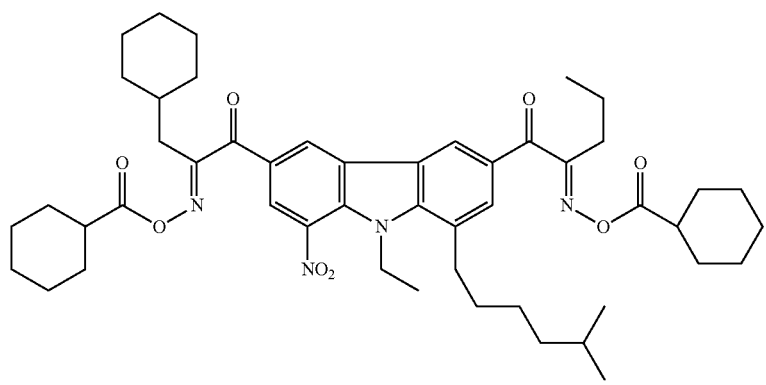
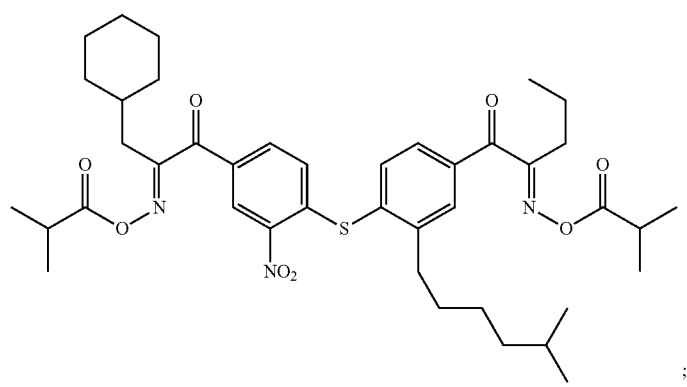

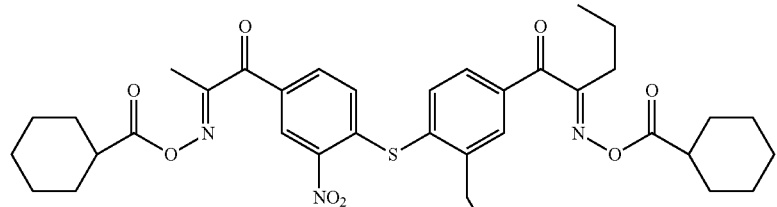
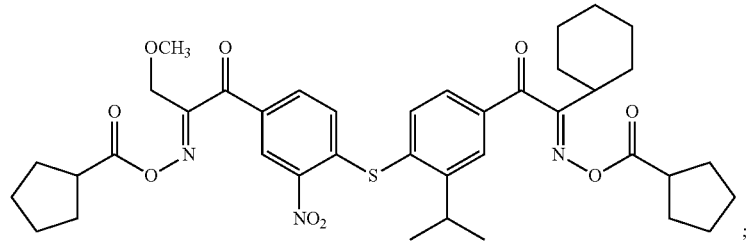
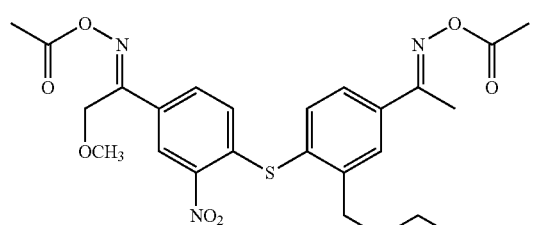
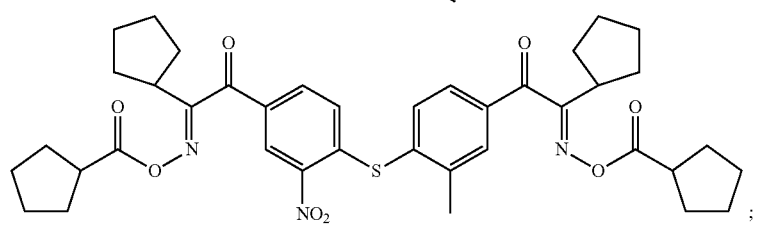
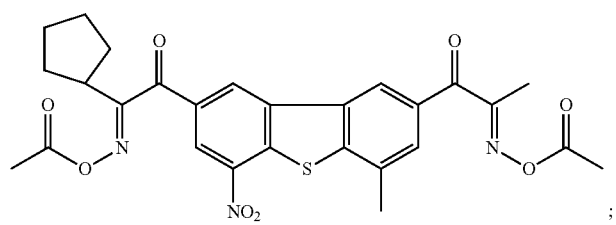
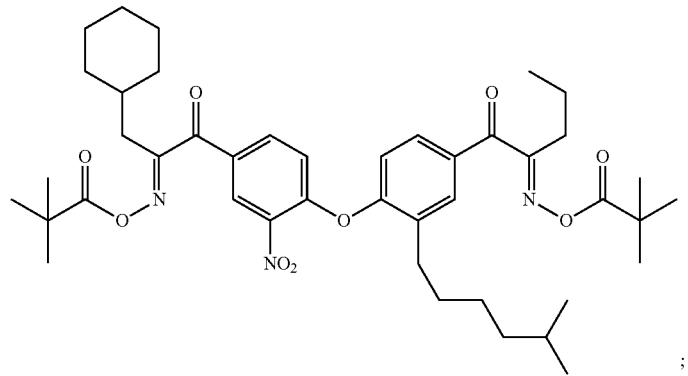

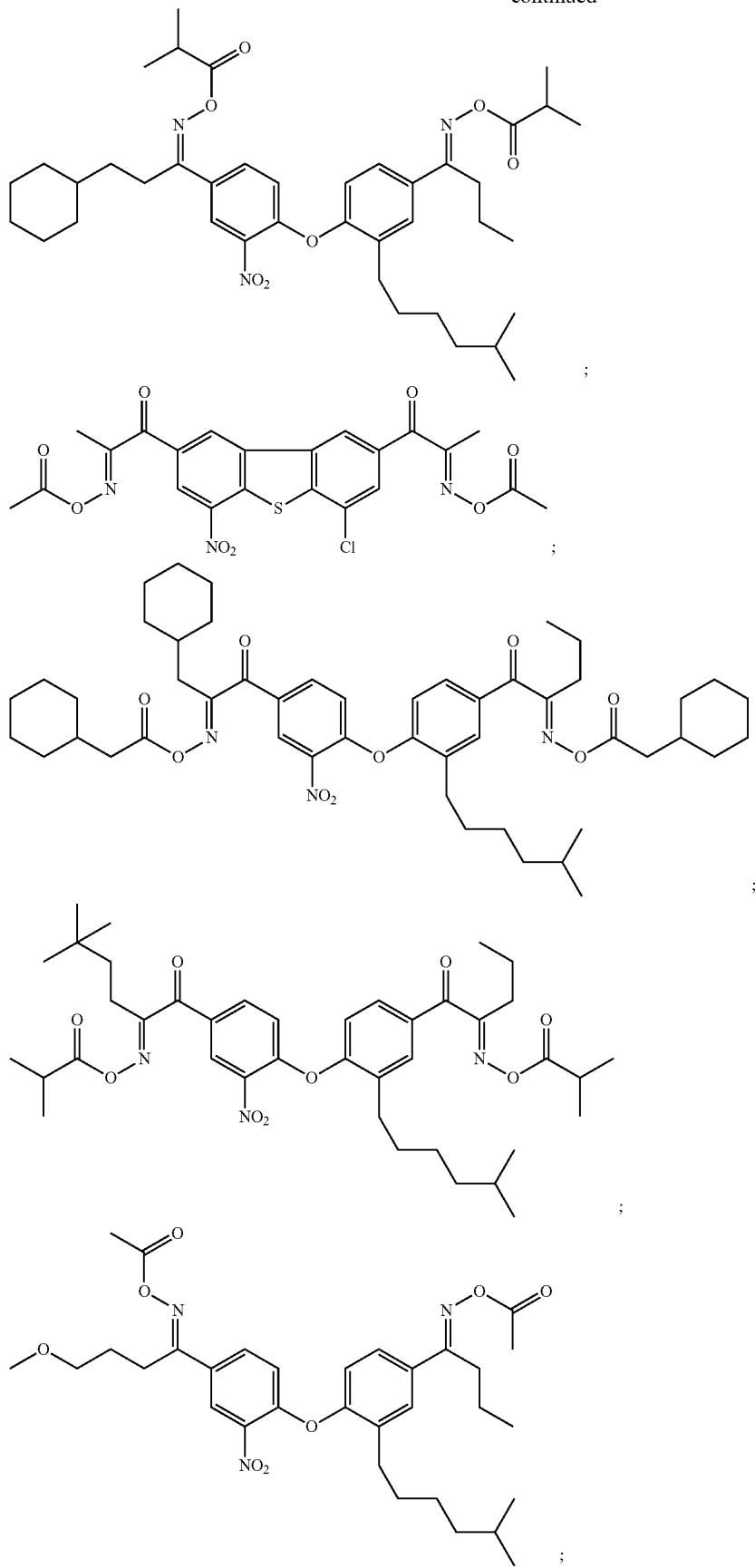

-continued

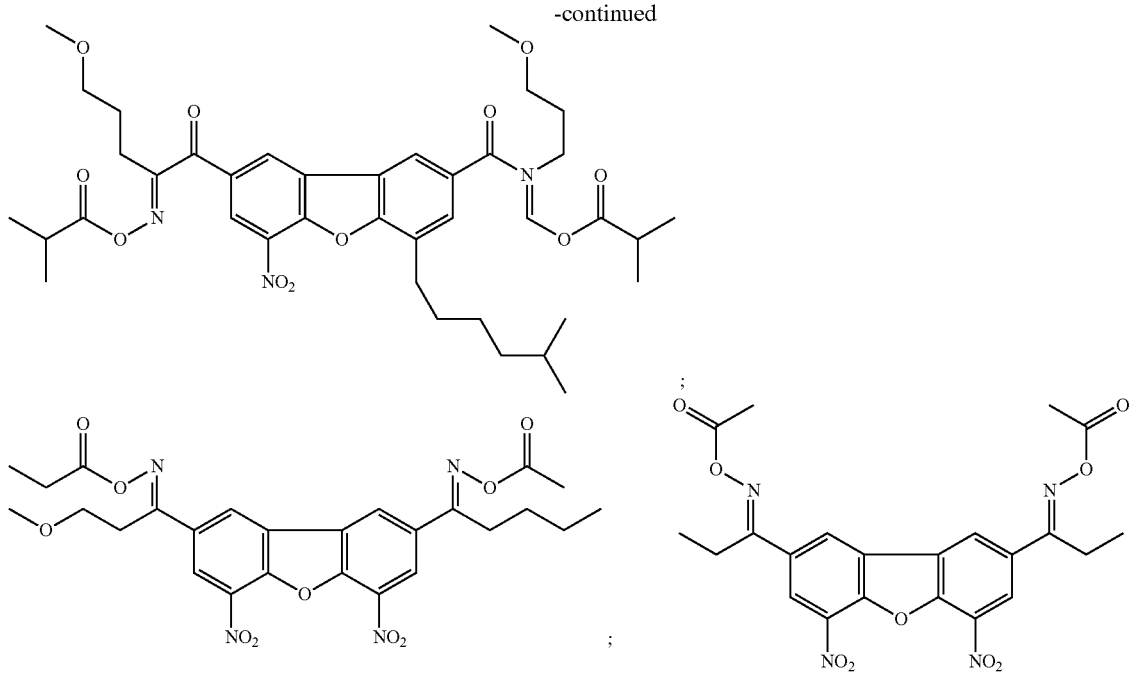

This invention also relates to a preparation method for the nitro-containing bisoxime ester photoinitiator represented by the general formula (I) described above, comprising: performing an esterification reaction between a compound containing a nitro-bisoximino group structure and a corresponding acid anhydride or acid halide to obtain a product of interest, and the specific reaction is as follows:

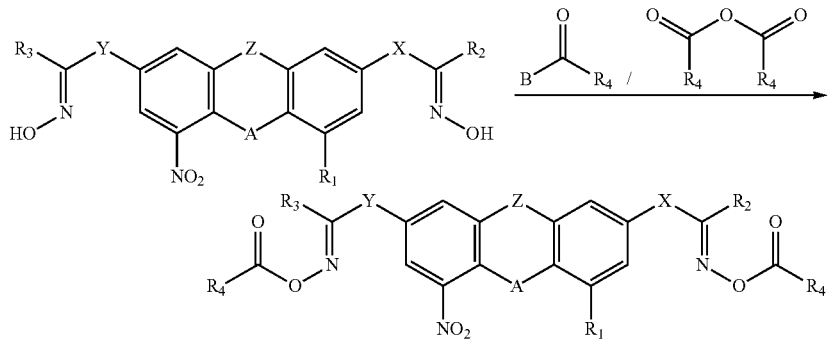

wherein, B represents halogen, such as F, Cl, Br, or I.

In the preparation method described above, all of the reaction materials are compounds which are known in the prior art, commercially available, or prepared by known synthetic methods. Here, the compound containing a nitro-bisoximino group structure,

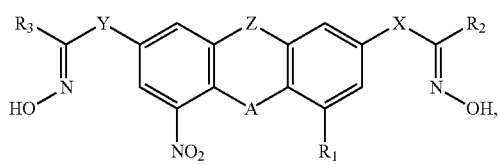

may be synthesized by a known technique disclosed in, for example, CN101565427B and CN102020727B. The preparation method disclosed by this invention has a simple process, does not produce polluted wastes, has high product purity, and is suitable for industrial production.

This invention also relates to use of the nitro-containing bisoxime ester photoinitiator represented by the general formula (I) described above in a photocurable composition (i.e., a photosensitive composition). Without limitation, this photoinitiator may be used in aspects such as color photoresists (RGB), black photoresists (BM), photo-spacers, dry films, semiconductor photoresists, inks, etc.

DESCRIPTION OF EMBODIMENTS

Hereafter, this invention will be further illustrated in conjunction with specific Examples, but it is not to be understood that the scope of this invention is limited thereto.

PREPARATION EXAMPLE

Example 1

Preparation of 1-nitro-3-(1-oxime acetate)propyl-6-(1-oxime acetate-3-cyclohexyl)propyl-9-ethyl-carbazole (compound 1)

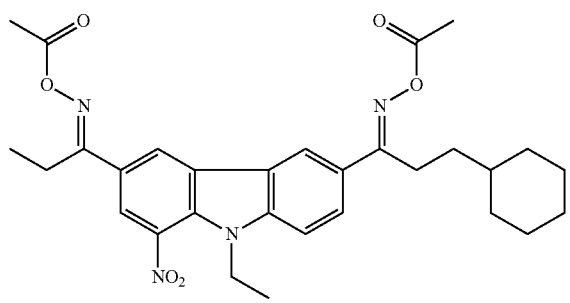

23.2 g of 1-nitro-3-(1-ketoxime)propyl-6-(1-ketoxime-3-cyclohexyl)propyl-9-ethyl-carbazole, 100 g of dichloromethane, and 5.1 g of triethylamine were added into a 250 mL four-neck flask and were stirred at room temperature for 5 min, and then 11.3 g of acetic anhydride was dropped within about 30 min. Stirring was continued at room temperature for 2 h, and then 5% $NaHCO_3$ aqueous solution was added to adjust pH value to become neutral. An organic layer was separated with a separation funnel, followed by washing twice with 200 mL of water and drying with 50 g of anhydrous $MgSO_4$, and the solvent was evaporated by rotation to obtain a viscous liquid. Recrystallization with methanol obtained a white solid powder, which was filtered to obtain a product of 24.7 g with a yield of 90% and a purity of 99%.

The structure of the product was determined by hydrogen nuclear magnetic resonance spectroscopy, and the specific characteristic result is as follows:

$^1$H-NMR(CDCl$_3$, 500 MHz): 0.9015-1.0102 (3H, t), 1.3918-1.4714 (13H, m), 1.5073-1.5932 (3H, t), 2.1022 (6H, s), 2.5468-2.7029 (4H, m), 3.8210-3.9421 (2H, m), 7.0301-7.8127 (3H, m), 8.4301-8.6127 (2H, s).

Example 2

Preparation of 1,8-dinitro-3-(1,2-dione-2-oxime-O-benzoate-3-cyclobutyl)propyl-6-(1,2-dione-2-oxime-O-benzoate)propyl-9-ethyl-carbazole (compound 2)

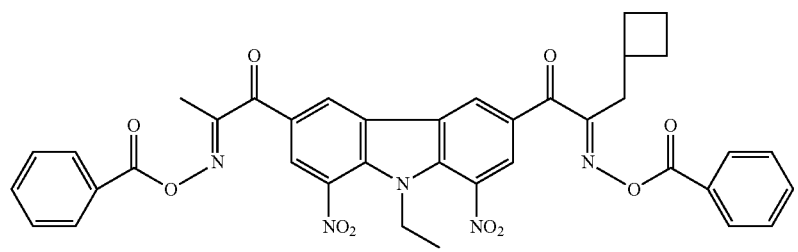

24.8 g of 1,8-dinitro-3-(1,2-dione-2-oxime-3-cyclobutyl)propyl-6-(1,2-dione-2-oxime)propyl-9-ethyl-carbazole, 100 g of dichloromethane, and 5.1 g of triethylamine were added into a 250 ml four-neck flask and were stirred at room temperature for 5 min, and then 14.3 g of benzoyl chloride was dropped within about 30 min. Stirring was continued at room temperature for 2 h, and then 5% $NaHCO_3$ aqueous solution was added to adjust pH value to become neutral. An organic layer was separated with a separation funnel, followed by washing twice with 200 mL of water and drying with 50 g of anhydrous $MgSO_4$, and the solvent was evaporated by rotation to obtain a viscous liquid. Recrystallization with methanol obtained a white solid powder, which was filtered to obtain a product of 20.9 g with a yield of 87% and a purity of 99%.

The structure of the product was determined by hydrogen nuclear magnetic resonance spectroscopy, and the specific characteristic result is as follows:

$^1$H-NMR(CDCl$_3$, 500 MHz): 1.4908-1.5193 (3H, t), 1.9037-2.1823 (7H, m), 2.5099-2.7629 (5H, m), 3.90732-4.0231 (2H, m), 7.4309-7.7098 (6H, t), 8.1067-8.2319 (4H, d), 8.3980-8.6678 (4H, s).

Examples 3-15

Referring to the method illustrated in Example 1 or 2, compounds 3-15 shown in Examples 3-15 were prepared from a corresponding compound containing a nitro-bisoximino group structure

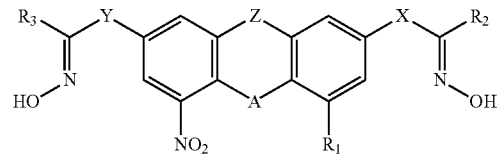

and an acid halide compound or an acid anhydride.

The structures of compounds of interest and $^1$H-NMR data thereof were listed in Table 1.

TABLE 1

| Examples | Compounds | $^1$H NMR δ[ppm] |
|---|---|---|
| Example 3 | Compound 3 | 1.4302-1.5547(12H,m)<br>2.1391(9H,s)<br>2.5349-2.6819(2H,d)<br>3.8790-3.9908(2H,m)<br>8.4450-8.7612(4H,s) |
| Example 4 | Compound 4 | 1.3908-1.5546(21H,m)<br>2.1987(6H,s)<br>2.6571-2.8719(4H,d)<br>3.7690-3.9908(2H,m)<br>8.3998-8.6971(4H,s) |
| Example 5 | Compound 5 | 0.9982-1.1034(6H,t)<br>1.3998-1.5051(13H,m)<br>1.7903-1.8234(2H,m)<br>2.0789 (6H,s)<br>2.6501-2.7836(4H,m)<br>3.7651-3.8957(2H,t)<br>8.2198-8.7891(4H,s) |
| Example 6 | Compound 6 | 1.0556-1.1239(6H,m)<br>1.4034-1.4689(11H,m)<br>1.7349-1.9734(3H,m)<br>2.1038(6H,s)<br>2.5987-2.8038(5H,m)<br>3.8890-3.9802(2H,d)<br>7.5298-8.6781(5H,m) |

TABLE 1-continued

| Examples | Compounds | ¹H NMR δ[ppm] |
|---|---|---|
| Example 7 | Compound 7 | 1.4098-1.5103(11H,m)<br>1.5203-1.7239(16H,m)<br>2.3452-2.4985(2H,m)<br>2.5617-2.8793(5H,m)<br>3.7721(3H,s)<br>7.4827-8.6723(5H,m) |
| Example 8 | Compound 8 | 1.3907-1.4572(11H,m)<br>1.5321-1.5932(3H,m)<br>2.4598-2.7893(5H,m)<br>3.8742-3.9804(2H,m)<br>7.4890-7.7693(9H,m)<br>8.0927-8.2186(4H,d)<br>8.4984-8.6739(2H,s) |
| Example 9 | Compound 9 | 1.4560-1.5237(14H,m)<br>2.5602-2.8739(5H,m)<br>3.8047-3.9901(2H,m)<br>7.4038-7.6566(6H,m)<br>8.0802-8.2231(4H,d)<br>8.3301-8.6902(4H,s) |
| Example 10 | Compound 10 | 1.4290-1.5545(14H,m)<br>2.5692-2.7178(5H,t)<br>3.8094-3.9842(2H,m)<br>7.4590-7.7345(9H,m)<br>8.0342-8.6783(6H,m) |
| Example 11 | Compound 11 | 1.4905-1.7037(24H,m)<br>2.3290-2.4012(2H,m)<br>2.4532(3H,s)<br>2.5632-2.7778(4H,m)<br>7.3089-8.5523(6H,m) |

TABLE 1-continued

| Examples | Compounds | $^1$H NMR δ[ppm] |
|---|---|---|
| Example 12 | Compound 12 | 1.4880-1.7112(9H,m)<br>2.1998(6H,s)<br>2.5779-2.7691(5H,m)<br>8.7099-8.9067(4H,s) |
| Example 13 | Compound 13 | 0.9987-1.1592(21H,m)<br>1.2308-1.3376(6H,m)<br>1.5065-1.5539(2H,m)<br>1.6450-1.8390(5H,m)<br>2.5609-2.7765(8H,m)<br>3.3011-3.4087(5H,m)<br>7.1028-8.5692(6H,m) |
| Example 14 | Compound 14 | 0.9982-1.1022(6H,t)<br>2.0899(6H,s)<br>2.6758-2.7746(4H,m)<br>8.5344-8.7892(4H,s) |
| Example 15 | Compound 15 | 0.9896-1.9212(6H,t)<br>2.1221(6H,s)<br>2.7636-2.7659(4H,m)<br>7.0344-8.6548(5H,m) |

Performance Evaluation

By formulating exemplary photocurable compositions, respective application performances of the photoinitiators represented by the formula (I) of this invention, were evaluated, including aspects of storage stability, photosensitivity, developability, pattern integrity, etc.

1. Formulation of Photocurable Compositions (1) Uncolored Photocurable Composition A

| | |
|---|---|
| Acrylate copolymer (Benzyl methacrylate/methacrylic acid/hydroxyethyl methacrylate (molar ratio of 70/10/20) copolymer (Mw: 10,000)) | 100 |
| Trimethylolpropane triacrylate (TMPTA) | 100 |
| Photoinitiator | 2 |
| Butanone (solvent) | 25 |

(2) Colored Photocurable Composition B

| | |
|---|---|
| Acrylate copolymer (Benzyl methacrylate/methacrylic acid/methyl methacrylate (molar ratio of 50/15/30) copolymer (Mw: 15,000)) | 100 |
| Dipentaerythritol hexaacrylate | 100 |
| Photoinitiator | 2 |
| Butanone (solvent) | 25 |
| Dye blue 15 | 5 |

In the compositions A and B described above, the photoinitiator was a nitro-containing bisoxime ester compound represented by the general formula (I) of this invention or a photoinitiator known in the prior art as a comparison, and the respective components were represented in parts by mass.

2. Development by Exposure (1) Development by Exposure after Film Coating Under Mercury Lamp Light Source The photocurable compositions A and B described above were stirred, respectively, under protection from light. Materials were taken on a PET template, film coating was performed with a wire bar, the solvent was removed by drying at 90° C. for 5 min, and a coating film with a film thickness of about 2 μm was formed. The substrate on which the coating film was formed was cooled to room temperature, a mask plate was attached thereon, and a long wavelength irradiation was achieved with a high pressure mercury lamp 1PCS light source through a FWHM color filter. Exposure was performed on the coating film through a seam of the mask plate under an ultraviolet having a wavelength of 370-420 nm. Subsequently, development was performed by soaking in a 2.5% sodium carbonate solution at 25° C. for 20 s, followed by washing with ultra-pure water and air drying. The pattern was fixed by hard baking at 220° C. for 30 min, and the obtained pattern was evaluated.

(2) Development by Exposure after Film Coating Under UV-LED Light Source

The photocurable compositions A and B described above were stirred, respectively, under protection from light. Materials were taken on a PET template, film coating was performed with a wire bar, the solvent was removed by drying at 90° C. for 5 min, and a coating film with a film thickness of about 2 μm was formed. The substrate on which the coating film was formed was cooled to room temperature, a mask plate was attached thereon, irradiation was performed with an LED point light source (model: UVEL-ET, Shenzhen Lamplic Technology Co., Ltd.), and exposure was performed on the coating film through a seam of the mask plate under a wavelength of 395 nm. Subsequently, development was performed by soaking in a 2.5% sodium carbonate solution at 25° C. for 20 s, followed by washing with ultra-pure water and air drying. The pattern was fixed by hard baking at 220° C. for 30 min, and the obtained pattern was evaluated.

3. Performance Evaluation of Photocurable Compositions (1) Storage Stability

After naturally storing a liquid-state photocurable composition at room temperature for 1 month, the degree of precipitation of substances was visually evaluated according to the following criteria:

A: No precipitation was observed;

B: Precipitation was slightly observed;

C: Significant precipitation was observed.

(2) Photosensitivity

Upon exposure, the minimum exposure amount of the irradiated region having a residual film rate of 90% or more after development in the step of exposure was evaluated as the demand of exposure. A smaller exposure demand represents a higher sensitivity.

(3) Developability and Pattern Integrity

The pattern on the substrate was observed using a scanning electron microscope (SEM) to evaluate the developability and the pattern integrity.

The developability was evaluated according to the following criteria:

○: No residue was observed in unexposed portions;

◉: A small amount of residue was observed in unexposed portions, but the residue is acceptable;

●: Significant residue was observed in unexposed portions.

The pattern integrity was evaluated according to the following criteria:

◇: No pattern defects were observed;

☐: A few defects were observed in some portions of the pattern;

◆: A number of defects were significantly observed in the pattern.

Evaluation results were as shown in Tables 2-5:

TABLE 2

Performance evaluation of photocurable composition A (Measurement of demand of exposure, developability, and pattern integrity under irradiation condition of mercury lamp light source)

| | Photoinitiator | Storage stability | Demand of exposure mJ/cm² | Developability | Pattern integrity |
|---|---|---|---|---|---|
| Example | Compound 1 | A | 52 | ○ | ◇ |
| | Compound 2 | A | 51 | ○ | ◇ |
| | Compound 5 | A | 51 | ○ | ◇ |
| | Compound 6 | A | 39 | ○ | ◇ |
| | Compound 9 | A | 33 | ○ | ◇ |
| | Compound 10 | A | 32 | ○ | ◇ |
| | Compound 12 | A | 35 | ○ | ◇ |
| | Compound 15 | A | 40 | ○ | ◇ |
| Comparative Example | Comparative compound 1 | A | 65 | ◉ | ☐ |
| | Comparative compound 2 | A | 60 | ◉ | ☐ |
| | Comparative compound 3 | A | 70 | ◉ | ☐ |
| | Comparative compound 4 | B | 105 | ◉ | ◆ |

TABLE 2-continued

Performance evaluation of photocurable composition A(Measurement of demand of exposure, developability, and pattern integrity under irradiation condition of mercury lamp light source)

| Photoinitiator | Storage stability | Demand of exposure mJ/cm$^2$ | Developability | Pattern integrity |
|---|---|---|---|---|
| Comparative compound 5 | B | 85 | ◉ | ◆ |
| Comparative compound 6 | C | 160 | • | ◆ |

TABLE 3

Performance evaluation of photocurable composition A(Irradiation of LED light source)

| | Photoinitiator | Demand of exposure mJ/cm$^2$ | Developability | Pattern integrity |
|---|---|---|---|---|
| Example | Compound 1 | 49 | ○ | ◇ |
| | Compound 2 | 36 | ○ | ◇ |
| | Compound 5 | 47 | ○ | ◇ |
| | Compound 6 | 47 | ○ | ◇ |
| | Compound 9 | 30 | ○ | ◇ |
| | Compound 10 | 29 | ○ | ◇ |
| | Compound 12 | 30 | ○ | ◇ |
| | Compound 15 | 34 | ○ | ◇ |
| Comparative Example | Comparative compound 1 | 270 | • | ◆ |
| | Comparative compound 2 | 254 | • | ◆ |
| | Comparative compound 3 | 300 | • | ◆ |
| | Comparative compound 4 | 368 | • | ◆ |
| | Comparative compound 5 | 312 | • | ◆ |
| | Comparative compound 6 | >500, still invalid | • | ◆ |

TABLE 4

Performance evaluation of photocurable composition B(Measurement of demand of exposure, developability, and pattern integrity under irradiation condition of mercury lamp light source)

| | Photoinitiator | Storage stability | Demand of exposure mJ/cm$^2$ | Developability | Pattern integrity |
|---|---|---|---|---|---|
| Example | Compound 1 | A | 57 | ○ | ◇ |
| | Compound 2 | A | 42 | ○ | ◇ |
| | Compound 5 | A | 54 | ○ | ◇ |
| | Compound 6 | A | 53 | ○ | ◇ |
| | Compound 9 | A | 36 | ○ | ◇ |
| | Compound 10 | A | 35 | ○ | ◇ |
| | Compound 12 | A | 36 | ○ | ◇ |
| | Compound 15 | A | 39 | ○ | ◇ |
| Comparative Example | Comparative compound 1 | A | 72 | ◉ | □ |
| | Comparative compound 2 | A | 68 | ◉ | □ |
| | Comparative compound 3 | A | 88 | ◉ | □ |
| | Comparative compound 4 | B | 117 | ◉ | ◆ |
| | Comparative compound 5 | B | 98 | ◉ | ◆ |
| | Comparative compound 6 | C | 176 | • | ◆ |

TABLE 5

Performance evaluation of photocurable composition B(Irradiation of LED light source)

| | Photoinitiator | Demand of exposure mJ/cm$^2$ | Developability | Pattern integrity |
|---|---|---|---|---|
| Example | Compound 1 | 50 | ○ | ◇ |
| | Compound 2 | 37 | ○ | ◇ |
| | Compound 5 | 48 | ○ | ◇ |
| | Compound 6 | 48 | ○ | ◇ |
| | Compound 9 | 30 | ○ | ◇ |
| | Compound 10 | 30 | ○ | ◇ |
| | Compound 12 | 32 | ○ | ◇ |
| | Compound 15 | 35 | ○ | ◇ |
| Comparative Example | Comparative compound 1 | 282 | • | ◆ |
| | Comparative compound 2 | 267 | • | ◆ |
| | Comparative compound 3 | 302 | • | ◆ |
| | Comparative compound 4 | 372 | • | ◆ |
| | Comparative compound 5 | 314 | • | ◆ |
| | Comparative compound 6 | >500, still invalid | • | ◆ |

In Tables 2-5, Comparative compound 1 represents a photoinitiator, 1-{4-[4-(2-thiophenecarbonyl)phenylthio]phenyl}-(3-cyclopentyl)-propane-1-ketoxime-O-acetate, disclosed in CN102492060A; Comparative compound 2 represents a photoinitiator, 1-[6-(2-thiophenecarbonyl)-9-ethylcarbazol-3-yl]-3-cyclopentyl-propane-1,2-dione-2-oxime-O-acetate, disclosed in CN103130919A; Comparative compound 3 represents a photoinitiator, 1-(6-o-methyl benzoyl-9-ethylcarbazol-3-yl)-(3-cyclopentylacetone)-1-oxime-acetate, disclosed in CN101508744A; Comparative compound 4 represents a photoinitiator, 1-(4-phenylthiophenyl)-octan-1,2-dione-2-oxime-O-benzoate, disclosed in CN1241562A; Comparative compound 5 represents a photoinitiator, 1-(6-o-methyl benzoyl-9-ethylcarbazol-3-yl)-(3-ethanone)-1-oxime-acetate, disclosed in CN1514845A; and Comparative compound 6 represents a commonly-used photoinitiator, 2-methyl-1-(4-methylthiophenyl)-2-morpholinyl-propane-1-one (commonly known as Irgacure907).

It can be seen from the results of Tables 2-5 that the photocurable compositions comprising the nitro-containing bisoxime ester photoinitiator represented by the general formula (I) of this invention have good storage stability, and either under the condition of conventional high-pressure mercury lamp light source or under the condition of UV-LED light source, these photocurable compositions (including colorless systems and pigment systems) exhibit extremely good photosensitivity, developability, and pattern integrity, and have excellent application effects. However, the six existing photoinitiators as comparisons have obvious shortages. They not only have no advantage under the excitation condition of mercury lamps, but also can be hardly matched with UV-LED light sources. Therefore, it is not possible to initiate polymerization or the efficiency for initiating polymerization is particularly low. The nitro-containing bisoxime ester photoinitiator represented by the general formula (I) of this invention has a photosensitive property, which is obviously superior to those of existing photoinitiators, under the irradiation of UV-LEDs having single wavelengths.

In summary, the nitro-containing bisoxime ester photoinitiator represented by the general formula (I) disclosed by this invention has excellent application performances and has good adaptability to UV-LED light sources, which can greatly improve performances of photocured products and has good promotion effects on the generalization and application of UV-LED light sources in the field of photocuring.

The invention claimed is:

1. A nitro-containing bisoxime ester photoinitiator, having a structure represented by general formula (I):

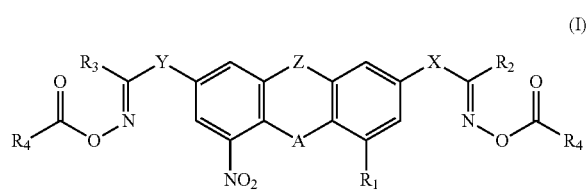

(I)

wherein
- X and Y each independently represent a carbonyl (—CO—) or a single bond;
- Z is blank, a single bond, or a $C_1$-$C_5$ alkylene group;
- A is O, S, or a $R_5N$— group, wherein $R_5$ represents hydrogen, a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group;
- $R_1$ represents hydrogen, halogen, a nitro group, a hydroxy group, a carboxyl group, a sulfonic acid group, an amino group, a cyano group, or an alkoxy group, or a $C_1$-$C_{20}$ linear or branched alkyl group, a $C_3$-$C_{20}$ cycloalkyl group, a $C_4$-$C_{20}$ cycloalkylalkyl group, or a $C_4$-$C_{20}$ alkylcycloalkyl group optionally substituted with one or more group selected from the group consisting of halogen, a nitro group, a hydroxy group, a carboxyl group, a sulfonic acid group, an amino group, a cyano group, and an alkoxy group;
- $R_2$ and $R_3$ each independently represent hydrogen, a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, or a $C_7$-$C_{20}$ aralkyl group, and optionally, hydrogen in the above groups may be substituted with a group selected from the group consisting of halogen, a nitro group, a hydroxy group, a carboxyl group, a sulfonic acid group, an amino group, a cyano group, and an alkoxy group;
- $R_4$ represents a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_3$-$C_{20}$ heteroaryl group, or a $C_6$-$C_{20}$ aryl group, and optionally, hydrogen in the above groups may be substituted with a group selected from the group consisting of halogen, a phenyl group, a nitro group, a hydroxy group, a carboxyl group, a sulfonic acid group, an amino group, a cyano group, and an alkoxy group.

2. The nitro-containing bisoxime ester photoinitiator according to claim 1, wherein Z is blank, a single bond, a methylene group, an ethylene, or a propylene group.

3. The nitro-containing bisoxime ester photoinitiator according to claim 1, wherein A is O, S, or a $R_5N$— group, wherein $R_5$ represents hydrogen, a $C_1$-$C_{10}$ linear or branched alkyl group, a $C_3$-$C_{15}$ cycloalkyl group, or a $C_4$-$C_{15}$ cycloalkylalkyl group.

4. The nitro-containing bisoxime ester photoinitiator according to claim 1, wherein $R_1$ represents hydrogen, halogen, a nitro group, or a $C_1$-$C_{15}$ linear or branched alkyl group.

5. The nitro-containing bisoxime ester photoinitiator according to claim 1, wherein $R_2$ and $R_3$ each independently represent hydrogen, a $C_1$-$C_{15}$ linear or branched alkyl group, a $C_3$-$C_{15}$ cycloalkyl group, a $C_4$-$C_{15}$ cycloalkylalkyl group, a $C_4$-$C_{15}$ alkylcycloalkyl group, or a $C_7$-$C_{15}$ aralkyl group, and optionally, hydrogen in the above groups may be substituted with a group selected from the group consisting of halogen, a nitro group, and an alkoxy group.

6. The nitro-containing bisoxime ester photoinitiator according to claim 1, wherein $R_4$ represents a $C_1$-$C_{10}$ linear or branched alkyl group, a $C_3$-$C_{10}$ cycloalkyl group, a $C_4$-$C_{10}$ cycloalkylalkyl group, a $C_4$-$C_{10}$ alkylcycloalkyl group, a $C_3$-$C_{10}$ heteroaryl group, or a $C_6$-$C_{10}$ aryl group.

7. The nitro-containing bisoxime ester photoinitiator according to claim 1, wherein the nitro-containing bisoxime ester photoinitiator is selected from the group consisting of the following structures:

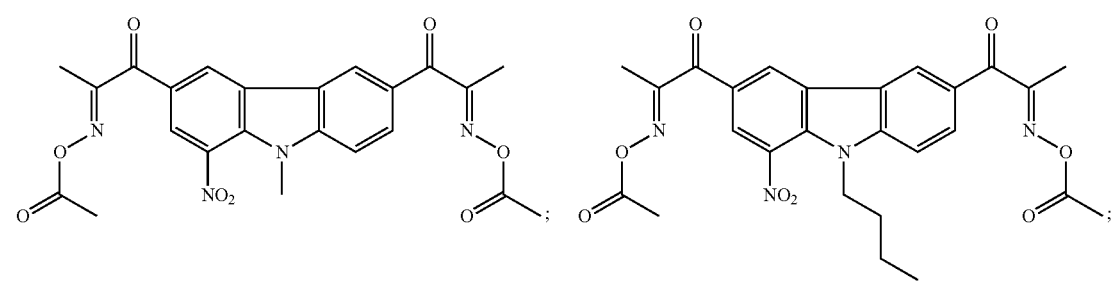

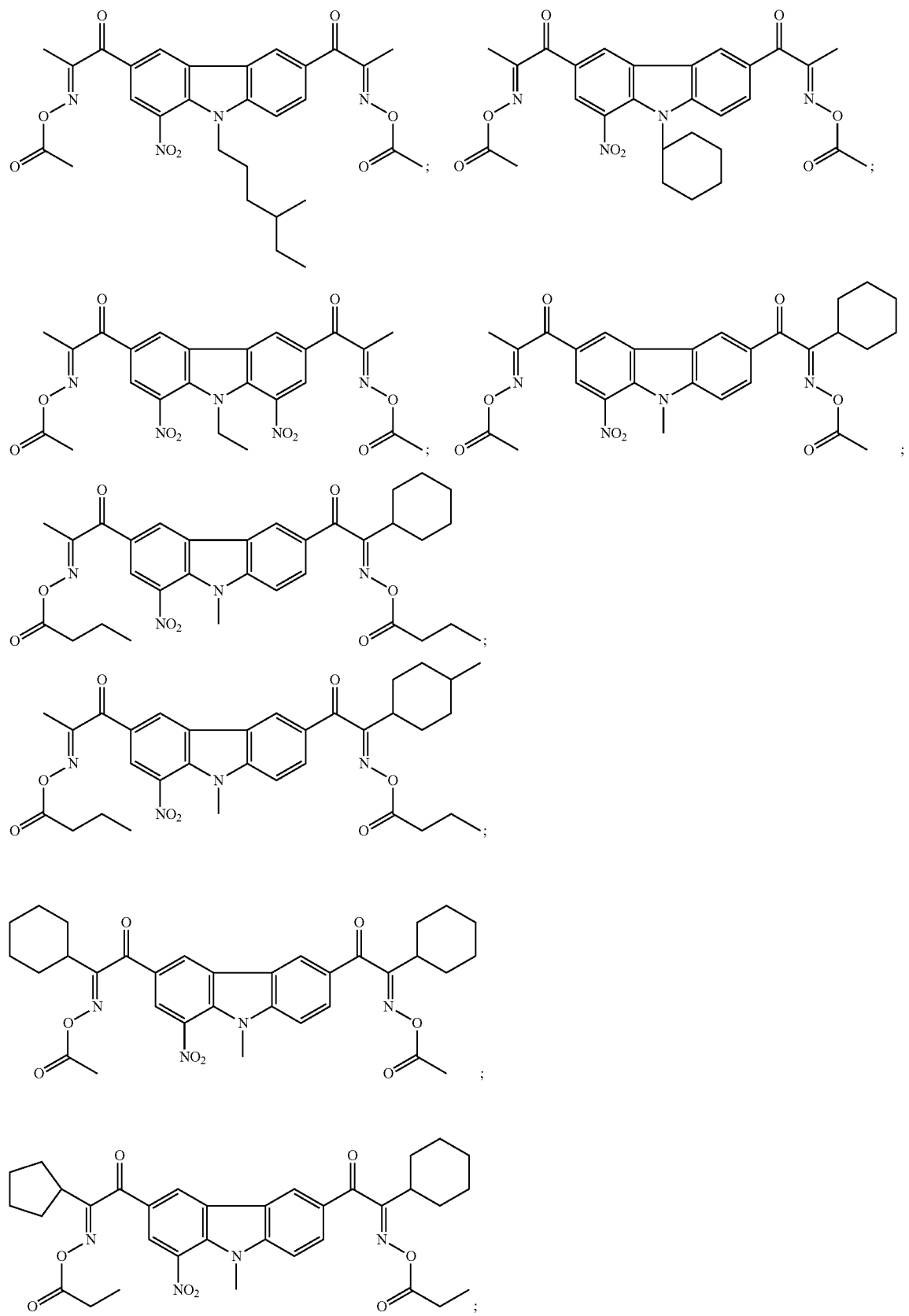

-continued
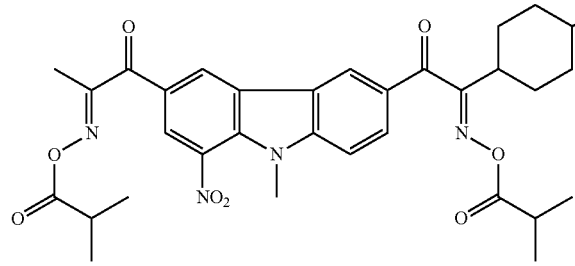
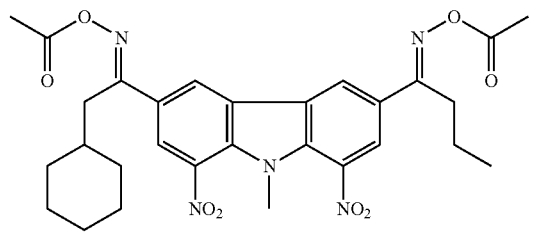
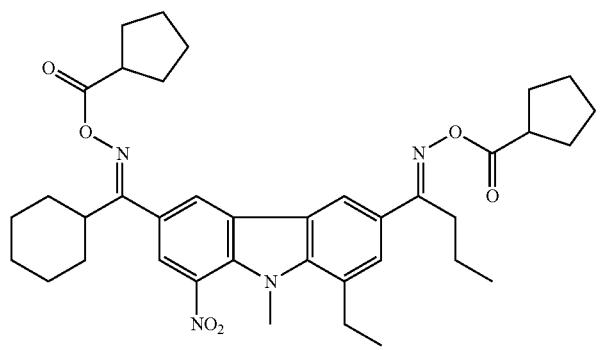
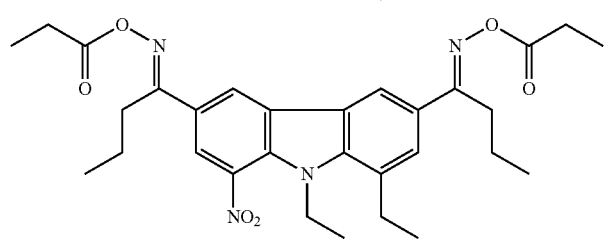
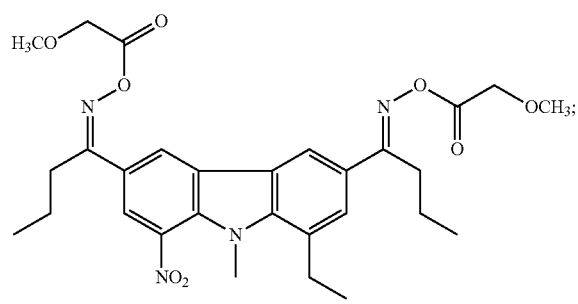
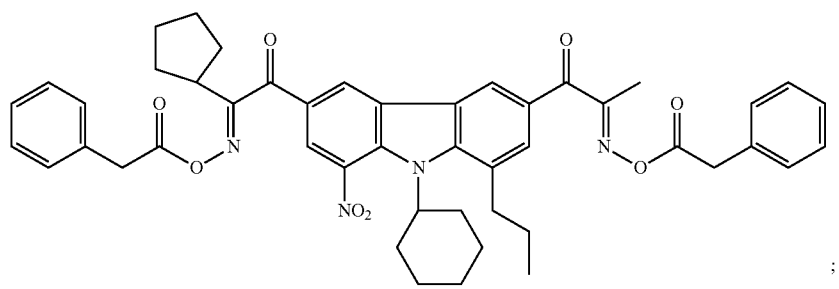
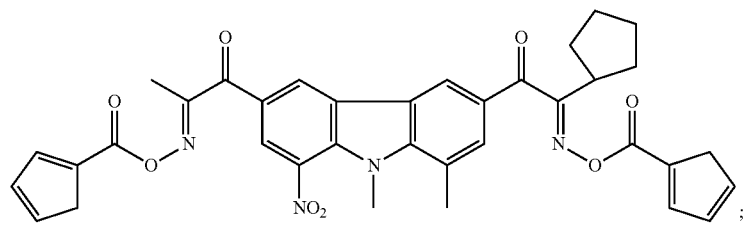

-continued
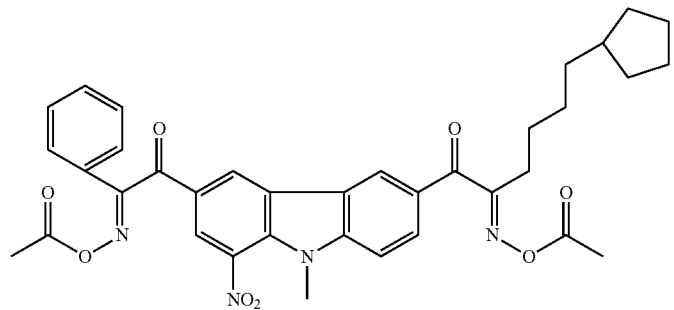
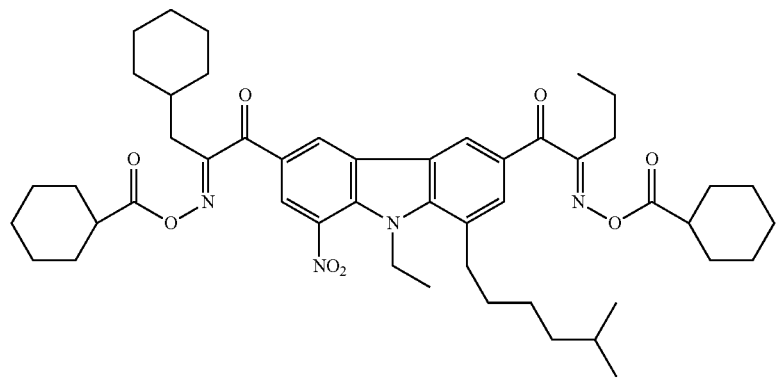
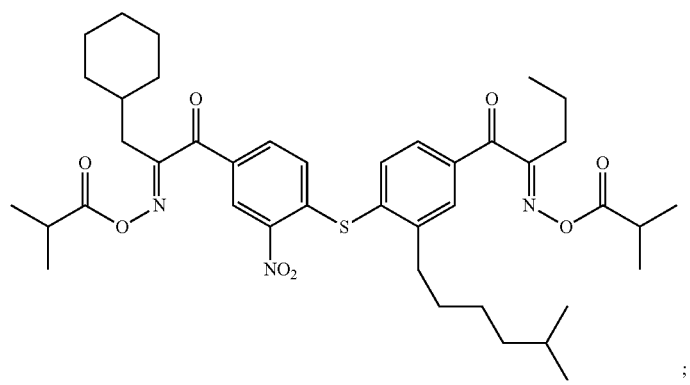
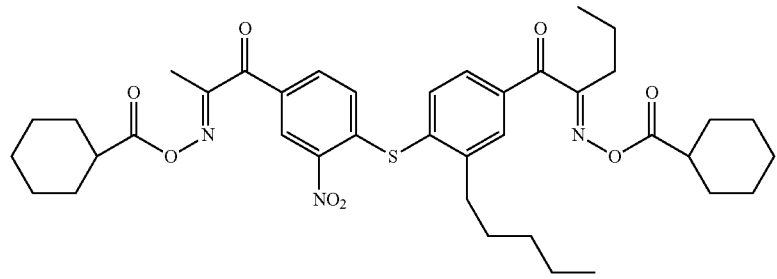
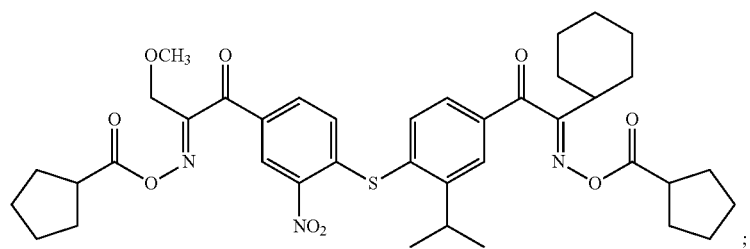

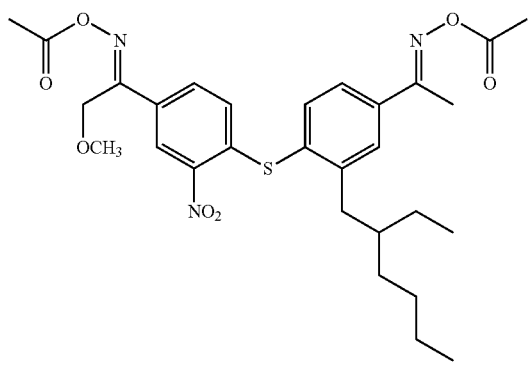
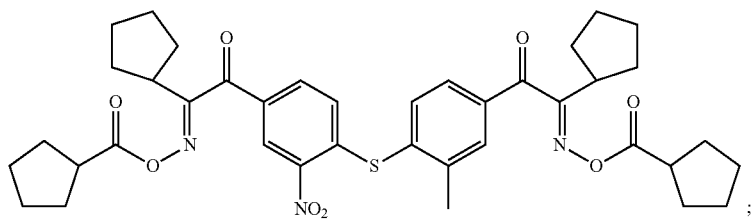
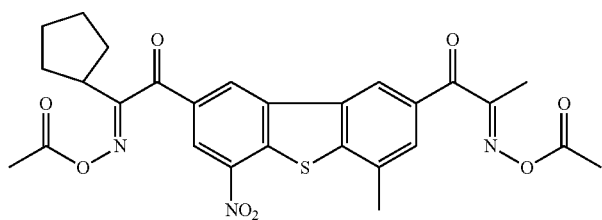
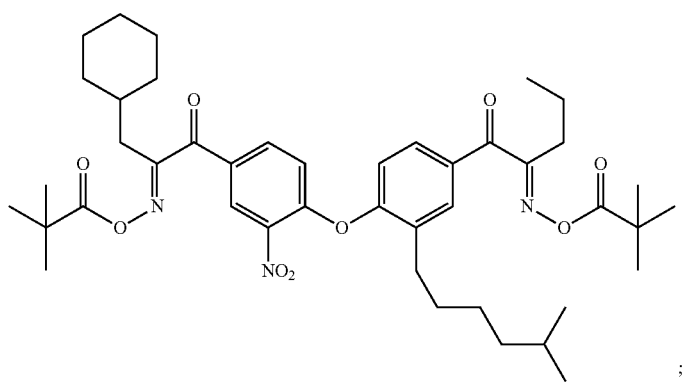
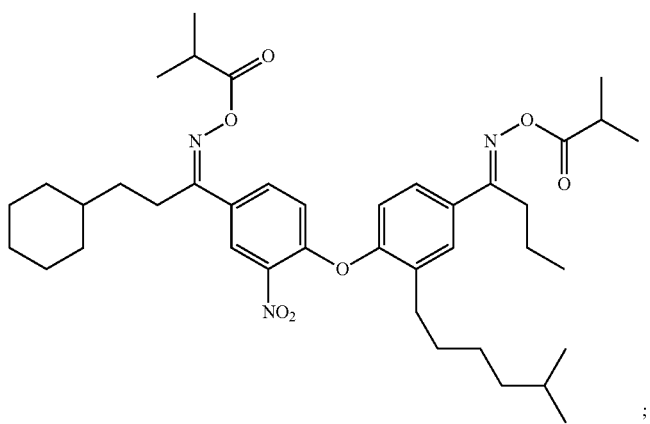

-continued
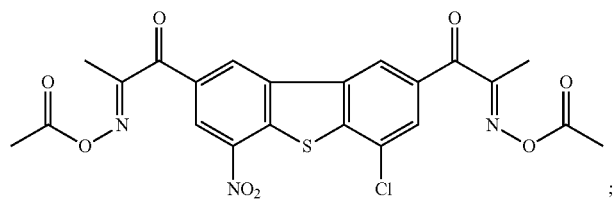;
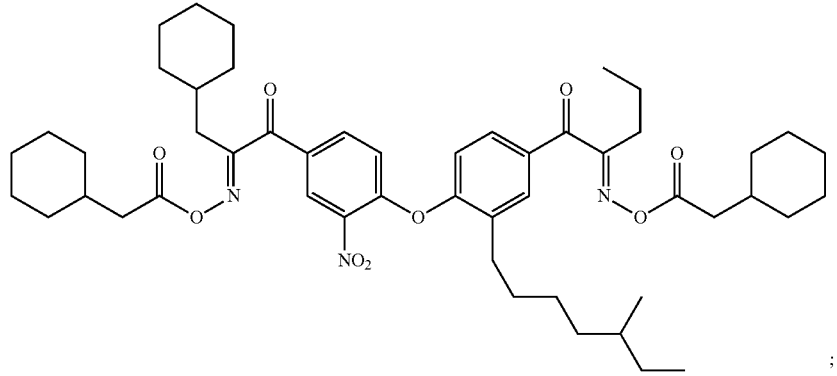;
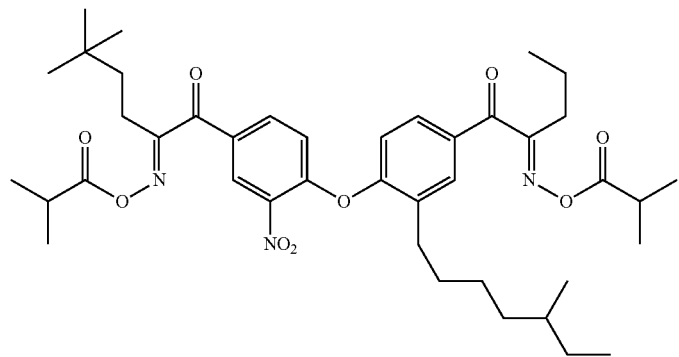;
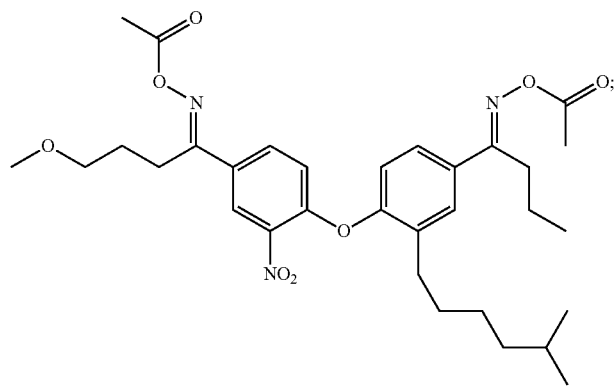;
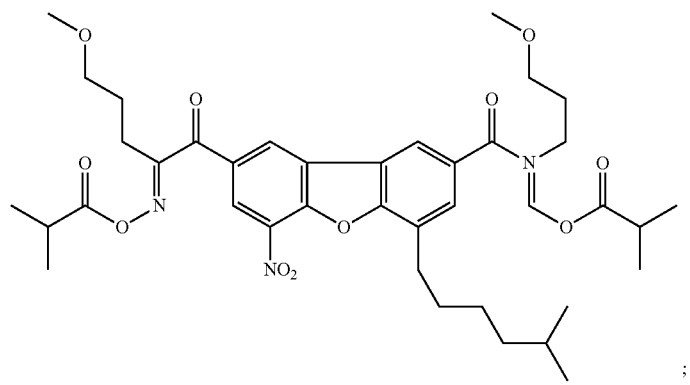;

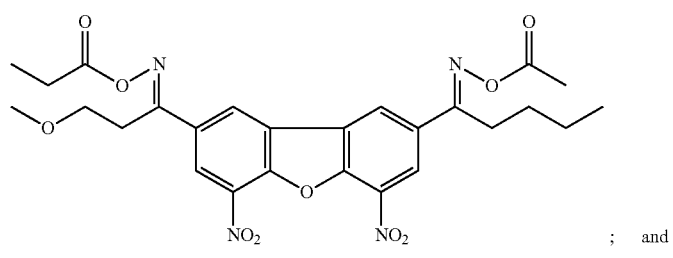

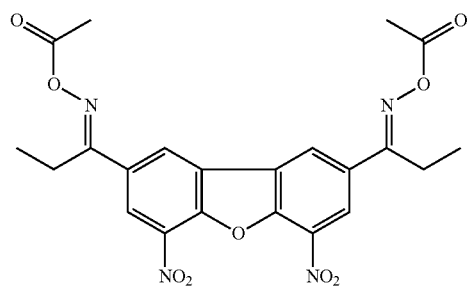

; and

8. A preparation method for the nitro-containing bisoxime ester photoinitiator of claim 1, comprising the step of:

performing an esterification reaction between a compound containing a nitro-bisoximino group structure and an acid anhydride or acid halide containing a $R_4$ group to obtain the nitro-containing bisoxime ester photoinitiator, the reaction shown as follows:

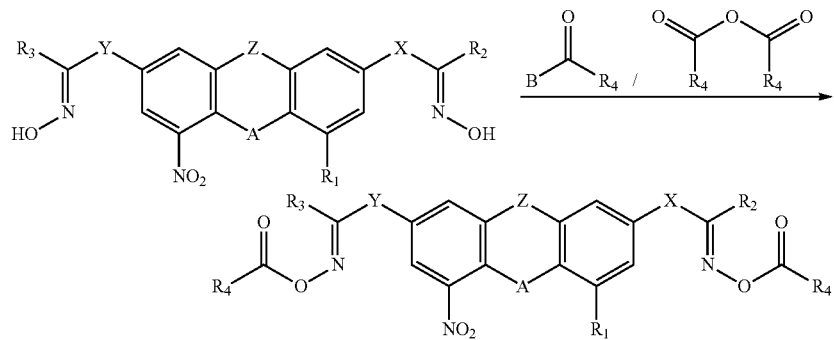

wherein B represents halogen.

* * * * *